US008333122B2

(12) United States Patent
Cosic et al.

(10) Patent No.: US 8,333,122 B2
(45) Date of Patent: Dec. 18, 2012

(54) DEVICE AND METHOD FOR APPLYING A FORCE TO A PLANAR SURFACE

(75) Inventors: Marijo Cosic, Offenbach am Main (DE); Stefan Scheller, Lorsch (DE); Thomas Malysa, Wiesbaden (DE)

(73) Assignee: UL LLC, Northbrook, IL (US)

( * ) Notice: Subject to any disclaimer, the term of this patent is extended or adjusted under 35 U.S.C. 154(b) by 322 days.

(21) Appl. No.: 12/849,425

(22) Filed: Aug. 3, 2010

(65) Prior Publication Data
US 2012/0031172 A1 Feb. 9, 2012

(51) Int. Cl.
G01L 1/02 (2006.01)
(52) U.S. Cl. .................................. 73/862.581
(58) Field of Classification Search ............. 73/862.581; 137/596.15
See application file for complete search history.

(56) References Cited

U.S. PATENT DOCUMENTS

| 3,423,995 A | 1/1969 | Scott et al. |
| 6,536,258 B1 | 3/2003 | Mostaghel |
| 6,691,580 B1 | 2/2004 | Bertelsen |
| 7,779,863 B2 * | 8/2010 | Jacobsen et al. ......... 137/596.15 |
| 2006/0021446 A1 | 2/2006 | England et al. |

FOREIGN PATENT DOCUMENTS

| DE | 115951 A1 | 10/1975 |
| DE | 102008024406 A1 | 11/2009 |

OTHER PUBLICATIONS

International Search Report and Written Opinion for Application No. PCT/US2010/045977, dated Apr. 28, 2011.

* cited by examiner

Primary Examiner — Jewel V Thompson
(74) Attorney, Agent, or Firm — Marshall, Gerstein & Borun LLP; Michael P. Furmanek

(57) ABSTRACT

A device for applying a force to a planar surface includes a tub, a cavity, a membrane, and an opening. The tub includes a bottom wall, at least one sidewall, and a cavity defined between the bottom and sidewalls. The membrane is disposed within the cavity and a perimeter edge of the membrane is fixed to the tub. The opening is formed in the tub and adapted to receive a pressurized fluid to fill a portion of the cavity below the membrane to displace at least a portion of the membrane away from the bottom wall to apply a force to the planar surface.

21 Claims, 5 Drawing Sheets

_DEVICE AND METHOD FOR APPLYING A FORCE TO A PLANAR SURFACE_

FIELD OF THE DISCLOSURE

The present disclosure relates to load generating devices and methods and, more particularly, to load generating devices and methods for applying a force to planar surfaces for testing the structural integrity of the planar surfaces and/or planar articles carrying the planar surfaces.

BACKGROUND

Photovoltaic modules (also referred to as "PV modules"), e.g., solar panels, are conventionally mounted in locations that are most prone to solar exposure. These locations include, for example, rooftops, open land, etc. Unfortunately, such locations are also exposed to snow, ice, wind, or other static and/or dynamic loads generated by the surrounding environment. A heavy snowfall or ice accumulation, or too strong a wind, can cause structural damage to the PV modules. Therefore, in an effort to ensure that commercially available PV modules can withstand the elements, manufacturers often test the designs in accordance with standardized testing procedures. In one known testing procedure, a number of sandbags are stacked onto the planar solar-exposed surface of a PV module for a specified period of time, for example. At the end of the specified period of time, the PV module is inspected for signs of physical damage.

SUMMARY

One aspect of the present disclosure provides a device for applying a force to a planar surface. The device includes a tub, a cavity, a membrane, and at least one opening. The tub has a bottom wall and at least one sidewall extending upward from a perimeter of the bottom wall. The cavity is defined between the bottom wall and the at least one sidewall of the tub. The membrane is disposed within the cavity at a location proximate to the bottom wall of the tub, and has a perimeter edge that is fixed to the tub. The opening is formed in the tub and adapted to receive a pressurized fluid to fill a portion of the cavity that is disposed between the membrane and the bottom wall to displace at least a portion of the membrane away from the bottom wall to apply a force to the planar surface during operation of the device.

In one aspect, the device can further comprise a bed of media disposed within the cavity on top of the membrane such that displacement of the membrane away from the bottom wall results in displacement of at least a portion of the bed of media away from the bottom wall and into engagement with the planar surface during operation of the device.

In one aspect, the bed of media can include a plurality of balls.

In one aspect, the bed of media can include three million plastic balls, each plastic ball having a diameter of approximately six millimeters.

In one aspect, the membrane can include an elastomeric material.

In one aspect, the device can further include at least one force sensor adapted to sense the force applied to the planar surface during operation of the device.

In one aspect, the device can further include a u-shaped bracket attached to the tub and suspending the at least one force sensor opposite the planar surface from the membrane, e.g., above the planar surface.

In one aspect, the device can further include at least one pressurized fluid source connected to the at least one opening in the tub for delivering pressurized fluid to the cavity.

In one aspect, the device can further include an electronic control unit communicatively coupled to the at least one force sensor and the pressurized fluid source for controlling and monitoring operation of the device.

In one aspect, the electronic control unit can include a user interface for receiving user input and/or displaying output.

In one aspect, the device can further include at least one adjustment panel horizontally disposed through the at least one sidewall of the tub and adapted to be adjusted to extend between the at least one sidewall and approximately a perimeter of the planar surface during operation of the device. In another aspect, the present disclosure provides a method for applying a force to a planar surface. The method includes positioning a planar surface above a membrane disposed within a cavity of a tub, wherein the cavity is defined between a bottom wall and at least one sidewall of the tub. The method further includes introducing a pressurized fluid into a portion of the cavity that is disposed between the bottom wall of the tub and the membrane. The method further includes displacing at least a portion of the membrane away from the bottom wall of the tub with the pressurized fluid. Finally, the method includes applying a force to the planar surface, the force being generated by the pressurized fluid and transferred through the membrane. In some aspects, positioning a planar surface above a membrane can include positioning the planar surface onto a bed of media disposed within the cavity and supported by the membrane.

In some aspects, the method further includes displacing at least a portion of the bed of media into engagement with the planar surface with the displaced membrane.

In some aspects, applying a force to the planar surface can include applying a force of a predetermined magnitude for a predetermined duration.

In some aspects, applying a force to the planar surface can include applying a force of uniform magnitude across the planar surface.

In some aspects, displacing at least a portion of the bed of media can include displacing a plurality of plastic balls into engagement with the planar surface.

In some aspects, introducing a pressurized fluid into a portion of the cavity can include delivering a pressurized gas into a portion of the cavity.

In some aspects, the method can further comprise detecting a magnitude of the force being applied to the planar surface with at least one force sensor.

In some aspects, the method can further comprise controlling a duration of the force being applied to the planar surface.

In some aspects, the method can further comprise inputting one or more of the following parameters into a user interface prior to introducing the pressurized fluid into the cavity: (a) a magnitude of the force to be applied to the planar surface; (b) a duration for which the force is to be applied to the planar surface; (c) a total number of cycles through which the force is to be applied the planar surface; and (d) a duration of any pause between cycles through which the force is to be applied to the planar surface.

DETAILED DESCRIPTION

Although the following text sets forth a detailed description of one or more embodiments of the invention, it should be understood that the legal scope of the invention is defined by the words of the claims set forth at the end of this patent. The detailed description is to be construed as exemplary only and does not describe every possible embodiment of the invention since describing every possible embodiment would be impractical, if not impossible. Numerous alternative embodiments could be implemented, using either current technology or technology developed after the filing date of this patent, which would still fall within the scope of the claims defining the invention.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term by limited, by implication or otherwise, to that single meaning. Finally, unless a claim element is defined by reciting the word "means" and a function without the recital of any structure, it is not intended that the scope of any claim element be interpreted based on the application of 35 U.S.C. §112, sixth paragraph.

In general, the device and method described herein are for generating a substantially uniform load, e.g., force, in a direction transverse to a two-dimensional plane for testing the structural integrity of a planar surface or a planar article such as a photovoltaic module (hereinafter "PV module"). Such tests are aimed at determining the ability of a PV module to withstand static and/or dynamic loads generated from wind, ice, snow, etc., and can be performed in accordance with various standardized testing protocols such as UL 1703 section 41, IEC 616215 section 10.16, and IEC 61646 section 10.16. While the device and method disclosed herein are generally designed for testing PV modules, they can also be used to test the structural integrity of other devices, or for any other foreseeable testing operation, manufacturing operation, or other function where a generally uniform load across a two-dimensional plane may be desired.

Figure 1:
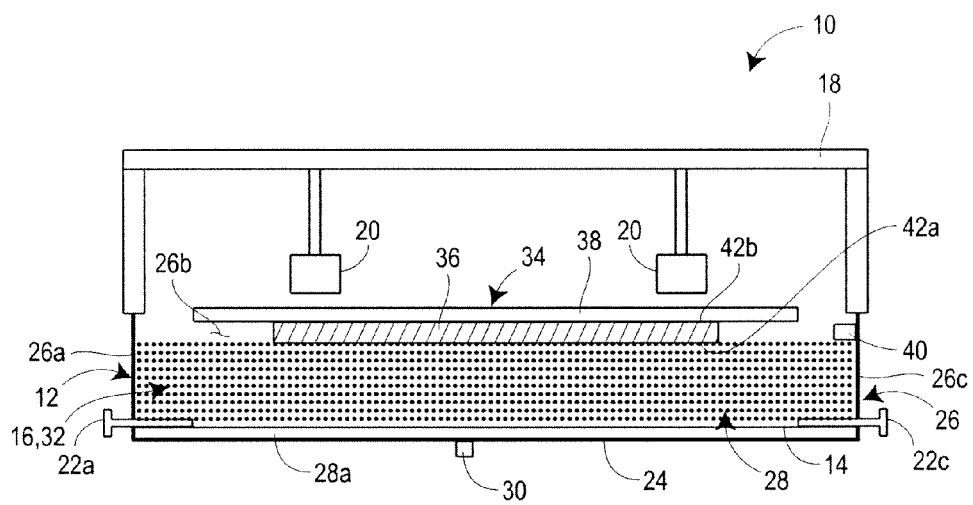
FIG. 1 is a schematic cross-sectional representation of one embodiment of a device for generating a load constructed in accordance with the present disclosure and shown occupying a passive state, e.g., non-operating state.
Figure 2:
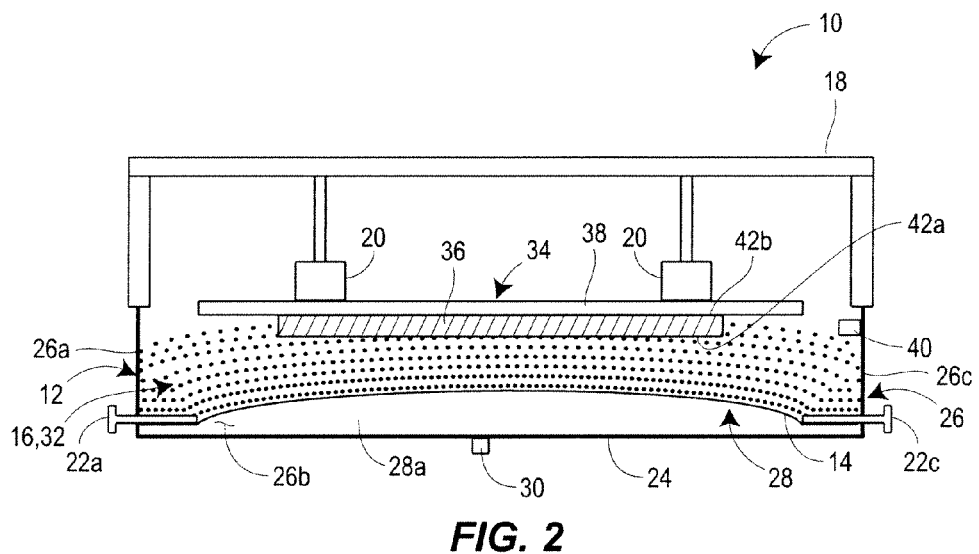
FIG. 2 is a schematic cross-sectional representation of the device of FIG. 1 shown occupying an active state, e.g., operating state.

FIGS. 1 and 2 include a pair of schematic cross-sectional representations of a device 10 constructed in accordance with the present disclosure. In FIG. 1, the device 10 is shown occupying a passive state, e.g., non-operating state. In FIG. 2, the device 10 is shown occupying an active state, e.g., operating state. As illustrated in FIGS. 1 and 2, one example of the device 10 can generally include a steel tub 12, a membrane 14, a bed of media 16, at least one overhead U-shaped bracket 18, and a plurality of force sensors 20. Additionally, as shown, one embodiment of the device 10 can include a plurality of adjustable panels 22 (only two panels 22a, 22c, of which are visible in FIGS. 1 and 2), at least one fluid opening 30, and a puller bar 40, each of which will be described in further detail below.

The tub 12 can generally resemble a box with an open top, for example, including a bottom wall 24, at least one sidewall 26 extending upward around a perimeter of the bottom wall 24, and a cavity 28 defined between the bottom wall 24 and the at least one sidewall 26. In the disclosed embodiment, the at least one sidewall 26 of the tub 12 includes four sidewalls 26a-26d, as shown more particularly in FIG. 3, such that the tub 12 has a generally square or rectangular shape when viewed from the top or bottom. In other embodiments, the tub 12 can have generally any shape when viewed from the top and/or bottom.

The membrane 14 includes a sheet of material disposed in the cavity 28 of the tub 12 proximate to the bottom wall 24, and mounted to the tub 12 to provide a generally fluid tight seal therebetween. In some embodiments, the membrane 14 can be mounted adjacent to its perimeter edge to the bottom wall 24 of the tub 12 with L-brackets or some other means, for example. In some other embodiments, the membrane 14 can be mounted adjacent to its perimeter edge to each of the sidewalls 26a-26d of the tub 12. So configured, the membrane 16 can be mounted at a height in the tub 12 so as not to contact the bottom wall 24 of the tub 12 when the device occupies the passive state, as shown in FIG. 1, for example. However, a certain amount of contact resulting from the membrane 12 sagging under the weight of the bed of media 16 can be acceptable. In one embodiment, the membrane 14 can be constructed of a substantially inelastic material, an elastic material, a flexible material, an elastomeric material, or generally any other type of material suitable for the intended purpose.

The bed of media 16 can include a plurality of balls 32 disposed in the tub 12 on top of the membrane 14. In one example, the plurality of balls 32 can include 3 million spherical plastic balls, each ball being approximately 6 millimeters in diameter. This is merely an example and other embodiments can include generally number and/or size of balls 32 suitable for the intended purpose. In other embodiments, the bed of media 16 can include generally any type of media capable of serving the intended purpose. For example, the bed of media 16 can include a plurality of objects having generally any shape, the objects being the same or different in shape, size, density, etc., or the bed of media 16 can include a fluid such as a liquid or a gas, or even a gel or other type of deformable mass. In one alternative embodiment, the device 10 could further include a second membrane (not shown) disposed opposite the bed of media 16 from the membrane 14, e.g., on top of the bed of media 16, such that the bed of media 16 is sandwiched between two membranes. Two membranes could be especially useful in an embodiment where the bed of media 16 includes a bed of fluid, for example, for retaining the fluid in the tub 12 both during operation and when the device 10 is non-operational.

The at least one overhead U-shaped bracket 18, as illustrated, carries the plurality of force sensors 20 such that the force sensors 20 are suspended above the bed of media 16 and the membrane 14 at a location opposite the bed of media 16 from the membrane 14.

Still referring to FIGS. 1 and 2, a planar article 36, which constitutes a PV module 34 in this example, is shown positioned in the device 10. In the disclosed embodiment, the PV module 34 includes a photovoltaic panel 36 (hereinafter "PV panel") mounted to a pair of roof brackets 38, only one of which is visible in FIGS. 1 and 2. Each of the roof brackets 38 includes a generally straight member mounted to the backside of the PV panel 36 parallel to the other roof bracket 38.

As shown, the PV module 34 is disposed in the tub 12 on top of the bed of media 16, and beneath the force sensors 20. In FIGS. 1 and 2, the roof brackets 38 face upward and are aligned with the force sensors 20, and a front planar surface 42a of the PV panel 36 faces downward and is in contact with the bed of media 16. So configured, the PV module 34 depicted in FIGS. 1 and 2 can be described as occupying an "upside-down" orientation.

Depending on the specific testing process being conducted, however, the PV module 34 could be turned over relative to the "upside-down" orientation to occupy a "right-side up" orientation. When disposed "right-side up," the front planar surface 42a of the PV panel 36 faces upward toward the force sensors 20 and the roof brackets 38 face downward and are in contact with the bed of media 16. So configured, the roof brackets 38 sink into, e.g., penetrate, the top surface of the bed of media 16 such that the bed of media 16 is in direct uniform contact with a rear planar surface 42b of the PV panel 36. In this "right-side up" orientation, the roof brackets 38 would still be aligned with the force sensors 20, but the force sensors 20 would instead be engaged by the PV panel 36.

In embodiments where the device 10 includes a second membrane on top of the bed of media 16 and wherein the PV module 34 is loaded "upside-down" (as shown in FIGS. 1 and 2), the front planar surface 42a of the PV panel 36 would be supported directly on the second membrane. In embodiments with a second membrane and where the PV module 34 is loaded "right-side up," the roof brackets 38 would necessarily deform the second membrane to enable the brackets 38 to sink into the bed of media 16. Such deformation of the membrane in the vicinity of the roof brackets 38 would preferably not limit the extent to which the bed of media 16 is capable of contacting the rear planar surface 42b PV panel 36 in a uniform manner.

Moreover, as mentioned above, the device 10 of the disclosed embodiment can be equipped with the plurality of adjustable panels 22. The plurality of panels 22 includes four adjustable panels 22a-22d, one slidably disposed through each of the four sidewalls 26a-26d. As shown in FIGS. 1 and 2, the panels 22 are positioned between the membrane 14 and the bed of media 16 in the vertical direction and between a perimeter of the PV module 34 and the sidewalls 26a-26d of the tub 12 in the horizontal direction. This configuration can limit the expansion and/or deflection of the membrane 14 during operation to the region located within the perimeter boundaries of the PV module 34.

For example, during operation of the device 10, a pneumatic line (not shown in FIGS. 1 and 2) is connected to the fluid opening 30 disposed in the bottom wall 24 of the tub 12 and a pressurized gas is introduced into a portion 28a of the cavity 28 that is disposed between the membrane 14 and the bottom wall 24. In some embodiments, gas is introduced at a pressure in the range of approximately 20 mbar to approximately 200 mbar. While the present embodiment of the tub 12 includes only a single opening 30, alternative embodiments can have a plurality of openings 30 spaced about the bottom wall 24, each being connected to its own pneumatic line. Such a configuration can increase the uniformity of the introduction of gas to the cavity. In any event, the pressurized gas causes at least the portion of the membrane 14 that is located between the adjustable panels 22a-22d to displace upwardly away from the bottom wall 24, as shown FIG. 2.

In some embodiments, displacement of the membrane 14 can result in the membrane 14 resiliently deforming, for example, by stretching similar to a balloon under the pressure of the gas delivered to the portion 28a of the cavity 28 of the tub 12. Regardless, displacement of the membrane 14 upward, in turn, causes the membrane 14 to displace at least a portion of the bed of media 16 upwardly away from the bottom wall 24 and into forceful engagement with 42a the PV panel 36 of the PV module 34 and, in the depicted embodiment, the front planar surface 42a of the PV panel 36. This force, in turn, displaces the PV module 34 upwardly away from the bottom wall 24 and into engagement with the force sensors 20 carried by the overhead U-shaped brackets 18. The force sensors 20 are adapted to detect the magnitude of the force being applied to the PV module 34. As mentioned, the bed of media 16 applies a generally uniform force across the PV panel 36 of the PV module 34, and in the depicted embodiment, across the front planar surface 42a of the PV panel 36. This uniform application of force is achieved because the bed of media 16 acts similar to a fluid in that in the disclosed embodiment, the three million plastic balls 32 move relative to each other to uniformly distribute the load applied by the membrane 14 through the balls 32 and onto the PV panel 36. Actual fluids and other types of media can operate similarly.

Figure 3:
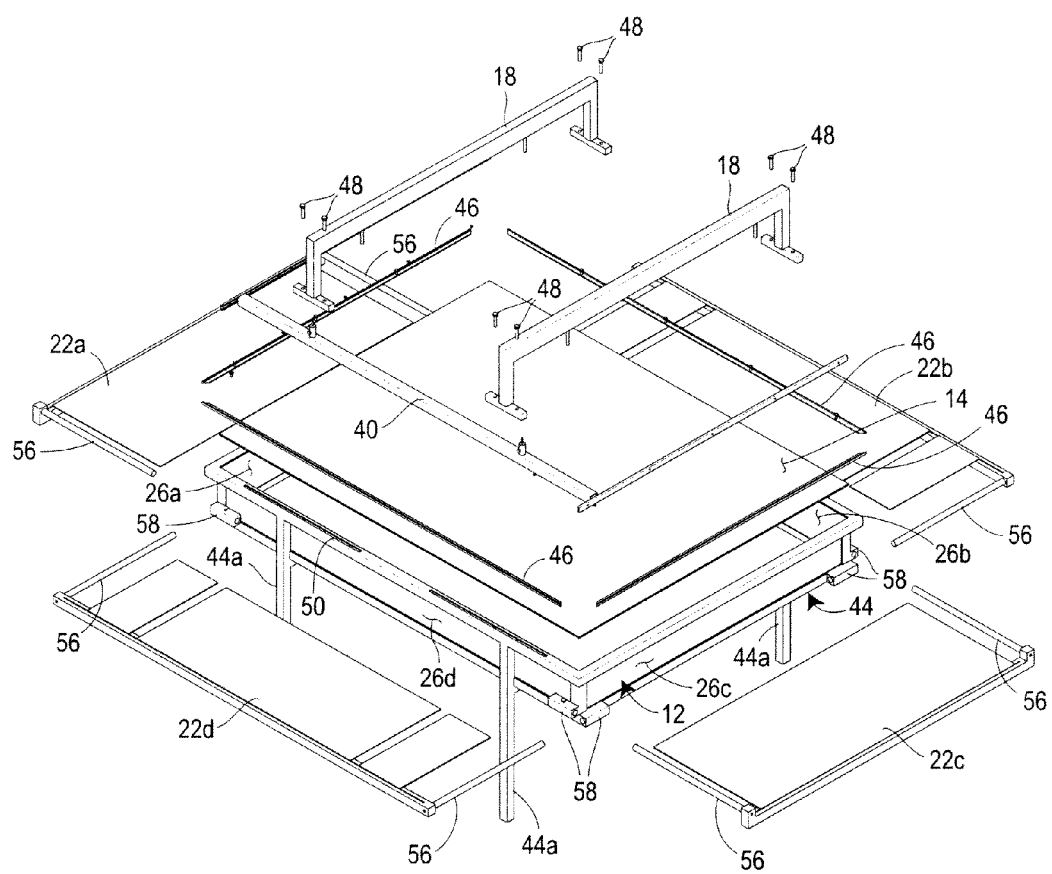
FIG. 3 is an exploded perspective view of some of the components of the device of FIGS. 1 and 2.

FIG. 3 depicts a specific construction of some of the components of one embodiment of the load generating device 10 of the present disclosure. For example, as shown in FIG. 3, in one embodiment, the steel tub 12 includes a frame 44 constructed of steel tubes and including legs 44a supporting the device on a floor, for example. The bottom wall 24 and the sidewalls 26a-26d are each constructed of a sheet metal material and can be welded or otherwise fixed to the frame 44. The membrane 14 is fixed into the tub 12, as shown generally in FIGS. 1 and 2, with a plurality of angle fixtures 46, which are shown in FIG. 3. Each angle fixture 46 can include an elongate metal member having an L-shaped cross-section, and which can be secured to the frame 44 of the tub 12 or directly to the bottom wall 24 or sidewalls 26a-26d of the tub 12 with screws, welding, rivets, or any other means, for example.

As shown in FIG. 3, each of the overhead U-shaped brackets 18 can be mounted with screws 48 to the topmost steel tube 50 of the frame 44. Preferably, the topmost tube 50 can include a plurality of different sets of holes for receiving the screws 48, such that the position of the overhead U-shaped brackets 18 can be adjusted to accommodate PV modules 34 having roof brackets 38 of different spacing.

As discussed above, the device 10 can include adjustable panels 22 for focusing the deflection of the membrane 14 to the area disposed between the perimeter boundaries of the PV module 34. The adjustable panels 22 can be adjusted by sliding horizontally through elongated openings (not shown) in the sidewalls 26a-26d of the tub 12. As depicted, the adjustable panels 22 include guide pins 56 disposed on opposing sides that are adapted to be slidably disposed in corresponding guide brackets 58 mounted on the outside of the tub 12, only some of which can be seen in FIG. 3. This sliding arrangement enables the position of the panels 22 to be adjusted in and out of the tub 12, thereby being adjustable to accommodate PV modules 34 of different dimensions. Preferably, a set screw (not shown) can be utilized to fix the position of each of the adjustment panels 22 prior to operating the device 12. In one embodiment, one set screw can be threaded through each of the guide brackets 58 to frictionally engage the corresponding guide pin 56, thereby locking the guide pins 56 and panels 22 in position.

Finally, as mentioned above with reference to FIGS. 1 and 2, the device 10 of the presently disclosed embodiment can include the puller bar 40. As shown in FIG. 3, the puller bar 40 constitutes an elongated bar adapted to be slidably mounted in the tub 12 at a height that corresponds to a top surface of the bed of media 16, as shown in FIGS. 1 and 2. So configured, after a loading operation is completed and the PV module 34 is removed from the tub 12, a technician can slide the puller bar 40 across the tub 12 to level the bed of media 16 in preparation for the next loading operation. Moreover, the device 10 can further be equipped with a vibrating mechanism such as a shaker table (not shown), for example, which can be activated when the PV module 34 is loaded right-side up, for example (i.e., when the roof brackets 38 are disposed in contact with the bed of media 16). With this orientation of the PV module 34, the vibrating mechanism can be activated to vibrate the bed of media 16 and/or the PV module 34 to obtain good displacement of the plastic balls 32 around the roof brackets 38 such that the balls 32 evenly distribute and uniformly contact the rear planar surface of the PV panel 36.

Figure 4:
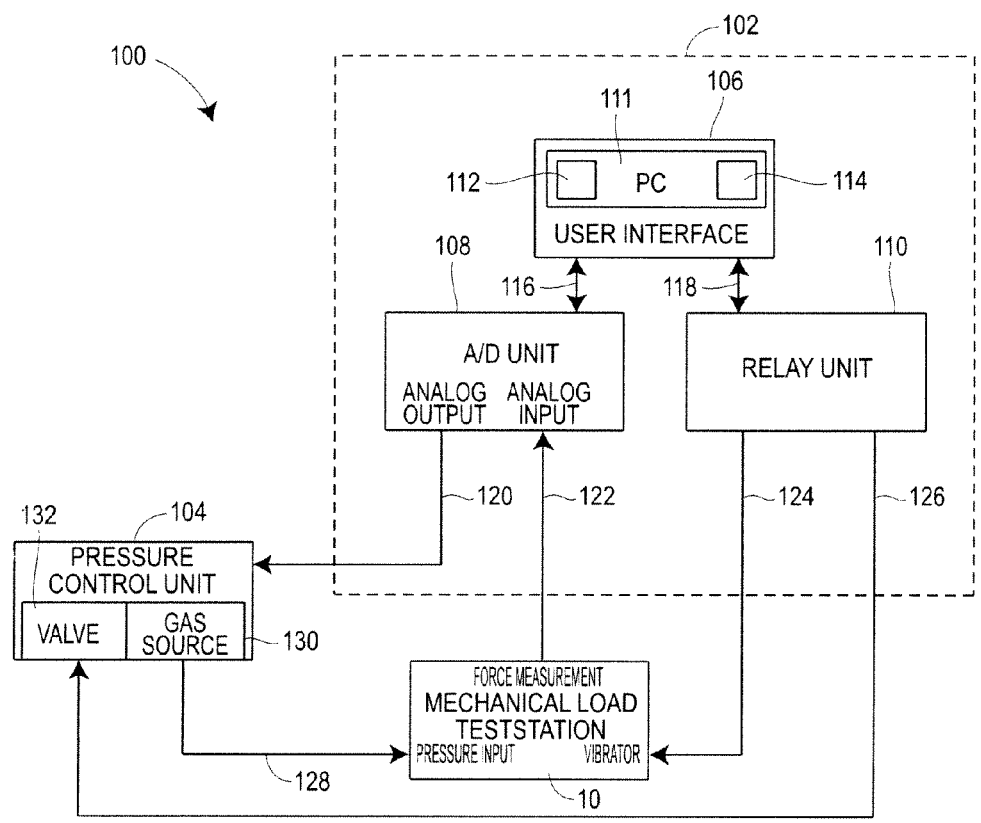
FIG. 4 is a block diagram of a system including the device of FIGS. 1-3 for applying a force to a planar surface.

As mentioned above, one application for the device 10 of the present disclosure is for testing the structural integrity of PV modules 34. To facilitate such tests, the device 10 can be incorporated into a system 100, as depicted in FIG. 4, for example. The system 100 of FIG. 4 includes the device 10, an electronic control unit 102, and a pressure control unit 104.

In the disclosed embodiment, the electronic control unit 102 can include a personal computer (hereinafter "PC") 106, an A/D unit 108, and a relay unit 110. The PC 106 can include a user interface 111 including, for example, an input device 112 such as a keyboard or touchscreen for enabling a user to input data into the PC 106, and an output device 114 such as a monitor, printer, speaker, or other device for conveying information to the user. Additionally, although not illustrated in FIG. 4, it should be appreciated that the PC 106 can include a processor, a RAM memory, a ROM memory, and/or any other component typically associated with a conventional computing device. The pressure control unit 104 includes at least one pressurized gas source 130 and at least one pressure control valve 132, for example. The A/D unit 108 includes a conventional analog/digital converter. The relay unit 110 acts as a conventional switch for controlling the flow of power to the load generating device 10 and the pressure control unit 104 in response to appropriate direction received from the PC 106.

As illustrated in FIG. 4, the PC 106 is communicatively coupled to the A/D unit 108 and the relay unit 110 via communication lines 116, 118, respectively. Moreover, as illustrated, the A/D unit 108 is communicatively coupled to the pressure control unit 104 via a communication line 120, and to the load generating device 10 via a communication line 122. In an embodiment, wherein the load generating device 10 includes a vibrating mechanism for evenly distributing the plastic balls 32 of the bed of media 16 around the roof brackets 38 of the PV module 34, as discussed above, the relay unit 110 can be communicatively coupled to the load generating device 10 via a power line 124. Additionally, the relay unit 110 is communicatively coupled to the pressure control unit 104 via a power line 126. Finally, the pressure control unit 104 includes a pneumatic line 128 connected to the load generating device 10 and, more particularly, to the fluid opening 30 in the bottom wall 24 of the tub 12 of the device 10, as discussed above with reference to FIGS. 1 and 2.

With reference now to the flowchart depicted in FIG. 5, a method of testing a PV module 34 will be described using the load generating device 10 and system 100 of FIGS. 1-4. First, at block 200, a user can enter data related to the forthcoming testing procedure into the PC 106 via the user interface 111. The data may include, for example, information indicative of the PV module 34 to be tested, information indicative of the test procedure to be performed, information indicative of the type and/or number of reports to be generated at the completion of the testing procedure, and/or any other foreseeable data.

Information indicative of the PV module 34 can include the dimensions of the PV module 34, the weight of the PV module 34, the material or materials of which the PV module 34 is constructed, the manufacturer of the PV module 34, the model number and/or serial number of the PV module 34, etc. Information indicative of the test procedure can include, for example, a magnitude of a target force to be applied to the PV module 34, a duration for which the target force is to be applied to the PV module 34, a total number of cycles through which the target force is to be applied to the PV module 34, a duration of any pause between cycles through which the target force is to be applied to the PV module 34, a pressure at which gas is delivered to the device 10 during operation, a velocity at which gas is delivered to the device 10 during operation, etc.

Figure 5:
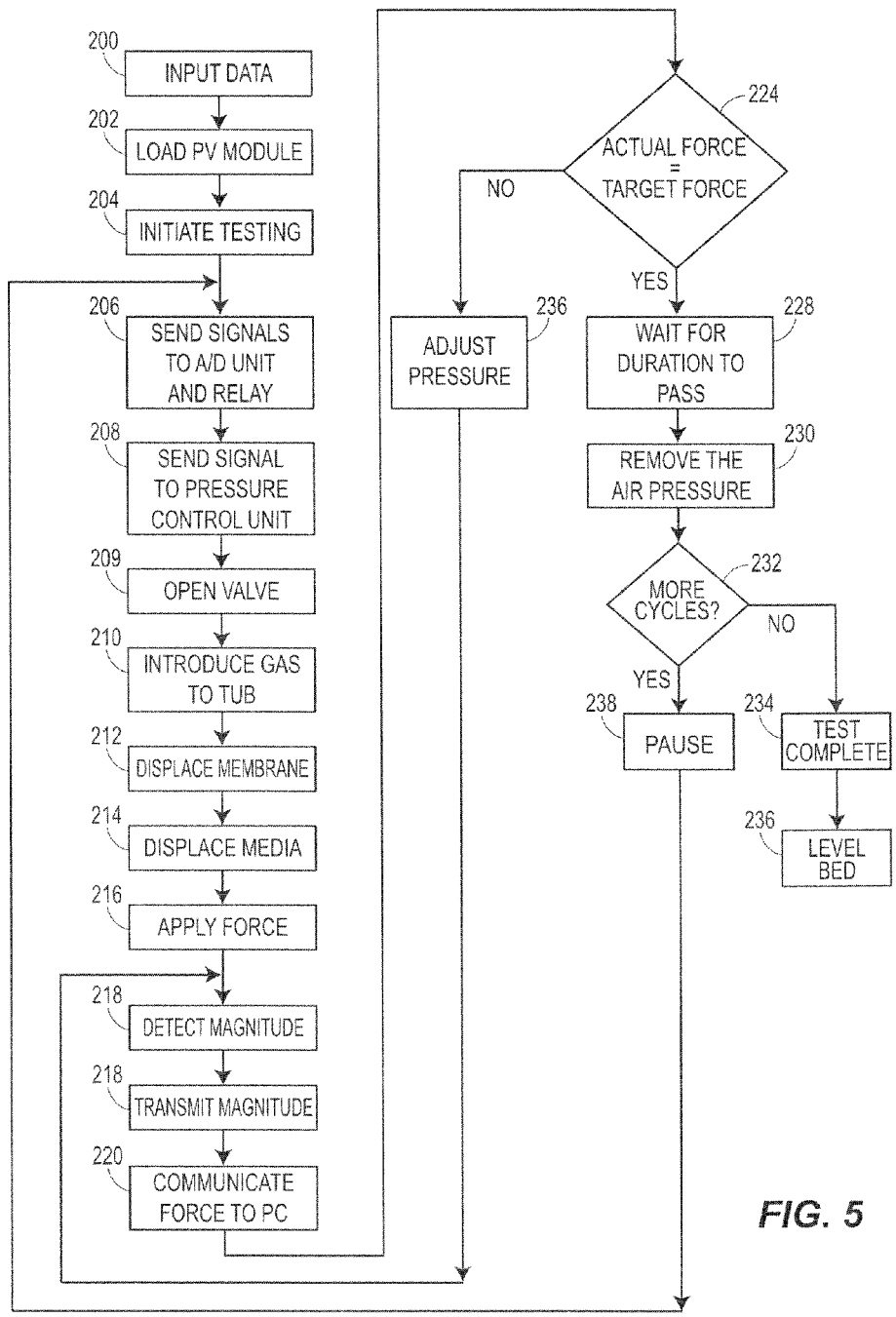
FIG. 5 is a flowchart of one method of the present disclosure for testing the structural integrity of a planar surface using the system of FIG. 4.

At block 202 of FIG. 5, the PV module 34 can be positioned upside-down into the tub 12 of the device 10 such that its front planar surface 42a is disposed in contact with the bed of media 16, as described above with reference to FIG. 1. Alternatively, block 202 can include positioning the PV module 34 into the tub 12 right-side up such that the roof brackets 38 and the rear planar surface 42b of the PV module 34 are disposed in contact with the bed of media 16. When the PV module 34 is positioned right-side up, block 202 can further include activating a vibrating mechanism, as discussed above, to evenly distribute the bed of media 16 around the roof brackets 38 and into contact with the rear planar surface of the PV panel 36. Specifically, block 202 can include the PC 106 sending a signal to the relay unit 110 over communication line 118 instructing the relay unit 110 to activate the vibrating mechanism by energizing power line 124 for a specified duration. Additionally, block 202 can include any desired adjustment of the position of the adjustable panels 22a-22d discussed above.

With the PV module 34 loaded into the tub 12, the PC 106 can initiate the testing procedure at block 204. At block 206, the PC 106 sends a digital signal to the A/D unit 108 over communication line 116 indicative of the initial force to be applied to the PV module 34, and sends a separate digital signal to the relay unit 110 over communication line 118 instructing the relay unit 110 to switch open the supply of power to the pressure control unit 104. At block 208, the A/D unit 108 converts the signal received from the PC 106 to an analog signal and transmits the analog signal to the pressure control unit 104 over communication line 120. At block 209, the energized pressure control unit 110 opens the control valve 132 to an extent that is based on the analog signal received from the A/D unit 108.

With the control valve 132 opened, pressurized gas flows from the pressurized gas source 130, through the pneumatic line 128, and into the portion 28a of the cavity 28 of the tub 12, as indicated at block 210 and described above with reference to FIGS. 1 and 2. As indicated at block 212, the pressurized gas causes the membrane 14 to displace upwardly away from the bottom wall 24 of the tub 12. The displacement of the membrane 14, in turn, causes at least a portion of the bed of media 16 to displace upwardly away from the bottom wall 24 of the tub 12, as indicated at block 214, and apply a force to the PV module 34, as indicated at block 216. The force applied to the PV module 34 is uniform across its two-dimensional surface and it displaces the PV module 34 into engagement with the force sensors 20 carried by the upper U-shaped brackets 18. The brackets 18 detect the magnitude of the force being applied to the PV module 34, as indicated at block 218. At block 220, each of the force sensors 20 transmit the detected forces to the A/D unit 108, or alternatively, the A/D unit 108 extracts the detected forces from each of the force sensors 20. At block 222, the A/D unit 108 converts the detected forces to one or more digital signals and transmits the signal(s) to the PC 106.

At block 224, the PC 106 determines whether the detected forces match the target force for the particular test procedure being conducted. If the forces do not match the target force, the PC 106 sends an adjusted digital signal to the A/D unit 108 at block 226, which then sends an adjusted analog signal to the pressure control unit 104 to adjust the opening of the control valve 132, which in turn, adjusts the amount of pressure being supplied to the tub 12 via pneumatic line 128. The process then returns to block 218.

In contrast, if the forces detected by the force sensors 20 match the target force, the PC 106 waits for a specified duration, as indicated at block 228. The specified duration corresponds to a duration dictated by the particular testing procedure being conducted, for example, or by the data input to the PC 106 at block 200 discussed above. At the end of the specified duration, the PC 106 sends a digital signal to the A/D unit 108 indicative of a close command, in response to which, the A/D unit 108 sends an analog signal to the pressure control unit 104 to close the pressure control valve 132 and stop supplying pressurized gas to the tub 12, as indicated at block 230. Simultaneously, any pressure built up in the tub 12 can be automatically vented through an exhaust valve (not shown) connected to the tub 12, for example, or through an exhaust valve associated with the pressure control valve 132 itself. At this point, the membrane 14 and bed of media 16 return to their passive state, shown in FIG. 1.

At block 232, it is determined if additional loading cycles are dictated by the particular testing procedure being conducted. If no additional loading cycles are desired, the testing procedure is complete, as indicated at block 234, and the PV module 34 can be removed from the device 10. Prior to loading a subsequent PV module 34 for testing, the bed of media 16 can be leveled, as indicated at block 236, through operation of the puller bar 40 discussed above. Alternatively, in embodiments wherein the load generating device 10 includes a vibrating mechanism, the vibrating mechanism could also be used to level the bed of media 16 between testing operations. In such a process, the PC 106 could send a signal to the relay unit 110 over communication line 118 instructing the relay unit 110 to activate the vibrating mechanism by energizing power line 124 for a specified duration to level the bed of media 16.

Alternatively, if additional loading cycles are desired or required to complete the testing procedure, the PC 106 waits for a designated pause duration, as indicated at block 238, prior to returning to block 206 to repeat the previously described process. Depending on the particular test being conducted, subsequent loading cycles may apply a force to the PV module 34 that is the same as or different from the magnitude previously applied. Moreover, subsequent loading cycles may apply a force to the PV module 34 for a duration that is the same as or different from the previous duration. The magnitude and duration of the force applied to the PV module 34 during each cycle of any testing procedure can be dictated and controlled by the electronic control unit 102 such that any give testing process is accurate and repeatable. Moreover, as mentioned, at the conclusion of any given testing process, the electronic control unit 102 of the present disclosure is advantageously capable of generating any number and/or style of reports related to the testing process including data, graphs, and analysis related to the magnitude and duration of the forces applied to the PV modules 34. Such reports could be generated on the display device 114 of the user interface 111 of the PC 106, saved to a memory, or printed in hard copy, for example.

Figure 6:
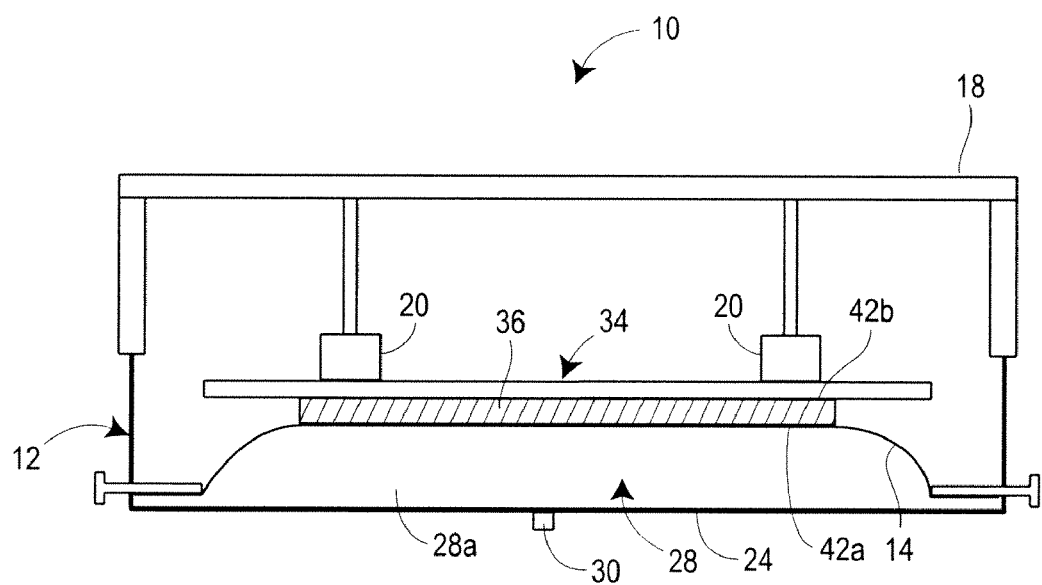
FIG. 6 is a cross-sectional representation of an alternative embodiment of a device for generating a load constructed in accordance with the principles of the present disclosure.

While the load generating device 10 of the present disclosure has thus far been described as including a bed of media 16 disposed on top of the membrane 14, at least one alternative embodiment of the device 10 can be constructed without the bed of media 16. For example, as illustrated in FIG. 6, one alternative load generating device 10 can include all of the features of the device 10 described above with reference to FIGS. 1-3, but for the bed of media 16. With this embodiment of the device 10, the introduction of pressurized gas into the portion 28a of the cavity 28 disposed below the membrane 14 causes the membrane 14 to displace or deflect upward and into direct engagement with a planar surface of a planar article being tested, which in FIG. 6 constitutes a front planar surface 42a of a PV panel 36 of a PV module 34. The displacement of the membrane 14 forcefully engages the PV module 34 and forces the PV module 34 into engagement with the force sensors 20 in a manner generally similar to that described above with reference to FIGS. 1-5. The device depicted in FIG. 6 could easily by used in the system described with reference to FIG. 4. Moreover, the method described above with reference to FIG. 5 could easily be adapted to be performed using the device 10 depicted in FIG. 6. The difference is that loading the PV module 34 into the device 10 of FIG. 6 simply includes positioning the PV module 34 directly on the membrane 14, and any force applied to the membrane 14 by the pressurized gas introduced through the opening 30 in the tub 12, would be transferred directly to the PV module 34 without distribution through the bed of media 16.

In view of the foregoing, it should be appreciated that the present disclosure advantageously provides among other advantages (a) a device capable of generating a uniform force across a two-dimensional planar surface; (b) a device that has the ability to generate detailed test results such as the magnitude of the force applied to the PV module, the duration of the test, the force carried by the roof brackets at the specific locations of the force sensors, etc.; and (c) the device and method enable a very quick, efficient, automated, and repeatable test procedure.

While the foregoing has described various embodiments, features, and components of a device and method for generating a load on a planar surface, the invention is not intended to be limited to the specifics described, but rather is intended to be defined by what a person having ordinary skill in the art would understand is the contribution to the art.

What is claimed:

1. A device for applying a force to a planar surface, the device comprising:
   a tub having a bottom wall and at least one sidewall extending upward from a perimeter of the bottom wall;
   a cavity defined between the bottom wall and the at least one sidewall of the tub;
   a membrane disposed within the cavity at a location proximate to the bottom wall of the tub, the membrane having a perimeter edge that is fixed to the tub;
   an opening formed in the tub, the opening adapted to receive a pressurized fluid to fill a portion of the cavity that is disposed between the membrane and the bottom wall to displace at least a portion of the membrane away from the bottom wall to apply a force to the planar surface during operation of the device.

2. The device of claim 1, further comprising a bed of media disposed within the cavity on top of the membrane such that displacement of the membrane away from the bottom wall results in displacement of at least a portion of the bed of media away from the bottom wall and into engagement with the planar surface during operation of the device.

3. The device of claim 2, wherein the bed of media comprises a plurality of balls.

4. The device of claim 2, wherein the bed of media comprises three million plastic balls, each plastic ball having a diameter of approximately six millimeters.

5. The device of claim 1, wherein the membrane comprises an elastomeric material.

6. The device of claim 1, further comprising at least one force sensor adapted to sense the force applied to the planar surface during operation of the device.

7. The device of claim 6, further comprising a u-shaped bracket attached to the tub and suspending the at least one force sensor opposite the planar surface from the membrane.

8. The device of claim 1, further comprising a pressurized fluid source connected to the opening in the tub for delivering pressurized fluid to the cavity.

9. The device of claim 8, further comprising an electronic control unit communicatively coupled to the at least one force sensor and the pressurized fluid source for controlling and monitoring operation of the device.

10. The device of claim 9, wherein the electronic control unit comprises a user interface for receiving user input and/or displaying output.

11. The device of claim 1, further comprising at least one adjustment panel horizontally disposed through the at least one sidewall of the tub and adapted to be adjusted to extend between the at least one sidewall and approximately a perimeter of the planar surface during operation of the device.

12. A method for applying a force to a planar surface, the method comprising:
    positioning a planar surface above a membrane disposed in a cavity of a tub, the cavity defined between a bottom wall and at least one sidewall of the tub;
    introducing a pressurized fluid into a portion of the cavity that is disposed between the bottom wall of the tub and the membrane;
    displacing at least a portion of the membrane away from the bottom wall of the tub with the pressurized fluid; and
    applying a force to the planar surface, the force being transferred through the membrane.

13. The method of claim 12, wherein positioning a planar surface above a membrane disposed in a cavity of a tub comprises positioning the planar surface onto a bed of media disposed within the cavity and supported by the membrane.

14. The method of claim 13, further comprising displacing at least a portion of the bed of media into engagement with the planar surface with the displaced membrane.

15. The method of claim 12, wherein applying a force to the planar surface comprises applying a force of a predetermined magnitude for a predetermined duration.

16. The method of claim 12, wherein applying a force to the planar surface comprises applying a force of uniform magnitude across the planar surface.

17. The method of claim 14, wherein displacing at least a portion of the bed of media comprises displacing a plurality of plastic balls into engagement with the planar surface.

18. The method of claim 12, wherein introducing a pressurized fluid into a portion of the cavity comprises delivering a pressurized gas into a portion of the cavity.

19. The method of claim 12, further comprising detecting a magnitude of the force being applied to the planar surface with at least one force sensor.

20. The method of claim 12, further comprising controlling a duration of the force being applied to the planar surface.

21. The method of claim 12, further comprising inputting one or more of the following parameters into a user interface prior to introducing the pressurized fluid into the cavity: (a) a magnitude of the force to be applied to the planar surface; (b) a duration for which the force is to be applied to the planar surface; (c) a total number of cycles through which the force is to be applied the planar surface; and (d) a duration of any pause between cycles through which the force is to be applied to the planar surface.

* * * * *